(12) United States Patent
Apt et al.

(10) Patent No.: US 6,399,383 B1
(45) Date of Patent: Jun. 4, 2002

(54) HUMAN PAPILLOMA VIRUS VECTORS

(75) Inventors: Doris Apt, Sunnyvale; Paul Khavari, Stanford; William P. C Stemmer, Los Gatos, all of CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/181,072
(22) Filed: Oct. 27, 1998

Related U.S. Application Data

(63) Continuation-in-part of application No. 08/958,822, filed on Oct. 28, 1997, now abandoned.

(51) Int. Cl.$^7$ .................. C12N 15/85; C12N 15/63; C12N 7/00; A61K 35/00; A61K 48/00
(52) U.S. Cl. .............. 435/456; 435/235.1; 435/320.1; 435/325; 424/93.1; 424/93.2; 514/44; 536/23.1
(58) Field of Search .............. 435/320.1, 325, 435/235.1, 456; 514/44; 424/93.2, 93.1; 530/350; 536/23.1

(56) References Cited

U.S. PATENT DOCUMENTS

| | | | |
|---|---|---|---|
| 5,605,793 A | 2/1997 | Stemmer | 435/6 |
| 5,811,238 A | 9/1998 | Stemmer et al. | 435/6 |
| 5,824,469 A | 10/1998 | Horwitz et al. | 435/6 |
| 5,830,721 A | 11/1998 | Stemmer et al. | 435/440 |
| 5,834,252 A | 11/1998 | Stemmer et al. | 435/91.1 |
| 5,837,458 A | 11/1998 | Minshull et al. | 435/6 |
| 5,928,905 A | 7/1999 | Stemmer et al. | 435/91.1 |
| 6,087,341 A | 7/2000 | Khavari et al. | 514/44 |
| 6,096,548 A | 8/2000 | Stemmer | 435/440 |

FOREIGN PATENT DOCUMENTS

| | | |
|---|---|---|
| WO | WO 95/22625 | 8/1995 |
| WO | WO 96/33207 | 10/1996 |
| WO | WO 97/20078 | 6/1997 |
| WO | WO 97/35957 | 10/1997 |
| WO | WO 97/35966 | 10/1997 |
| WO | WO 98/13485 | 4/1998 |
| WO | WO 98/13487 | 4/1998 |
| WO | WO 98/27230 | 6/1998 |
| WO | WO 98/31816 | 7/1998 |
| WO | WO 98/31837 | 7/1998 |
| WO | WO 99/21979 | 5/1999 |
| WO | WO 99/23107 | 5/1999 |
| WO | WO 99/29902 | 6/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/51774 | 10/1999 |
| WO | WO 99/57128 | 11/1999 |
| WO | WO 99/65927 | 12/1999 |
| WO | WO 00/04190 | 1/2000 |
| WO | WO 00/06718 | 2/2000 |
| WO | WO 00/09682 | 2/2000 |
| WO | WO 00/09727 | 2/2000 |
| WO | WO 00/12680 | 3/2000 |
| WO | WO 00/18906 | 4/2000 |
| WO | WO 00/20573 | 4/2000 |

OTHER PUBLICATIONS

Plumpton et al., "A High Capacity Assay for Inhibitors of Human Papillomavirus DNA Replication," *BioTechnology*, 13:1210–1214 (1995).
Adey et al., "Preparation of second–generation phage libraries," from *Phage Disp. Pept. Proteins*, eds. Kay et al., pp. 277–291 (1996).
Affholter et al., "Directed evolution of proteins and pathways by DNA shuffling," from *Book of Abstracts*, 216th ACS National Meeting, Boston, Aug. 23–27, 1998, BIOT–042.
Crameri et al., "10(20)–Fold Aptamer Library Amplification Without Gel Purification," *Nuc. Acids Res.*, 21(18):4410 (1993).
Crameri et al., "DNA shuffling of a family of genes from diverse species accelerates directed evolution," *Nature*, 391:288–291 (1998).
Crameri et al., "Molecular evolution of an arsenate detoxification pathway by DNA shuffling," *Nature Biotech.*, 15:436–438 (1997).
Crameri et al., "Improved green fluorescent protein by molecular evolution using DNA shuffling," *Nature Biotech.*, 14:315–319 (1996).
Crameri et al., "Construction and evolution of antibody–phage libraries by DNA shuffling," *Nature Medicine*, 2:100–103 (1996).
Crameri et al., "Combinational multiple cassette mutagenesis creates all the permutations of mutant and wildtype cassettes,", *Biotechniques*, 18:194–195 (1995).
Gates et al., "Affinity selective isolation of ligands from peptide libraries through display on a lac repressor 'headpiece dimer'," *J. Molecular Biology*, 255:373–386 (1996).
Howard, R.J., "Chemistry of the Future: Exploitation of the power of biology," from Book of Abstracts, 16th ACS National Meeting, Boston, Aug. 23–27, 1998, BTEC–045.
Patten et al., "Applications of DNA Shuffling to Pharmaceuticals and Vaccines," *Curr. Opin. Biotechnology*, 8:724–733 (1997).

(List continued on next page.)

Primary Examiner—Michael C. Wilson
(74) Attorney, Agent, or Firm—Joe Liebeschuetz; Scott Ausenhus; Margaret A. Powers

(57) ABSTRACT

The invention provides human papillomavirus vectors useful in gene therapy. Such a vector contains E1 and E2 coding regions from a benign or low-risk human papillomavirus operably linked to a promoter and enhancer, and an LCR region from a human papillomavirus comprising an origin of replication including binding sites for the E1 and E2 proteins. The invention further provides methods of using such vectors in gene therapy, methods of controlling expression using a patch, and methods of using such vectors to evolve drugs for stimulation of hair growth or alteration of hair color.

40 Claims, 7 Drawing Sheets

OTHER PUBLICATIONS

Punnonen et al., "Evolution of Genetic Vaccines by DNA Shuffling," from Keystone Symposium on Molecular Aspects of Viral Immunity, Tamarron, CO, Feb. 16–22, 1998, abstract 227.

Punnonen et al., "Evolution of DNA Vaccine Vectors by DNA Shuffling," from The First Gordon Conference on Genetic Vaccines/DNA Vaccines, Plymouth State College, Plymouth, NH, Jul. 20–25, 1997.

Soong et al., "DNA Shuffling as a Tool to Evolve Desired Retroviral Phenotypes," from Gene Therapy, 1998 meeting, Sep. 23–27, 1998, abstract p. 228, Cold Spring Harbor Laboratory, Cold Spring Harbor, New York.

Soong et al., "Directed Evolution of Novel Retroviral Tropisms bt DNA Shuffling," Abstract 97, Programs and Abstracts, 1st Annual Meeting of the American Society of Gene Therapy, May 28–31, 1998, Seattle, WA.

Soong et al., "Directed Evolution of Novel Retroviral Tropisms by DNA Shuffling," Abstract, Retroviruses, 1998 meeting, May 26–31, 1998, Cold Spring harbor laboratory, Cold Spring Harbor, New York.

Stemmer et al., "Sexual PCR and Assembly PCR," from *Encyclopedia of Molecular Biology*, VCh Publishers, New York, pp. 447–457 (1996).

Stemmer et al., "The Evolution of Molecular Computation," *Science*, 270:1510 (1995).

Stemmer et al., "Single–step assembly of a gene and entire plasmid from large numbers of oligodeoxyribonucleotides," *Gene*, 164(1):49–53 (1995).

Stemmer, W.P.C., "Searching Sequence Space," *BioTechnology*, 13:549–553 (1995).

Stemmer, W.P.C., "DNA shuffling by random fragmentation and reassembly: In vitro recombination for molecular evolution," *PNAS*, 91:10747–10751 (1994).

Stemmer, W.P.C., "Rapid evolution of a protein in vitro by DNA shuffling," *Nature*, 370:389–391 (1994).

Stemmer, W.P.C., Directed evolution of proteins, pathways, episomes and viruses by DNA shuffling,*FASEB J.*, 12(8):A1303, from Meeting of the American Society for Biochemistry and Molecular Biology, Washington, D.C., May 16–20, 1998.

Stemmer et al., "Molecular evolution of genes and pathways by DNA shuffling," *FASEB J.*, 11(9):A1124, from 17th Int. Congress of Biochem. and Mol. Biol. in conjunction with Annual Meeting of American Society for Biochem. and Mol. Biol., San Francisco, CA, Aug. 24–29, 1997.

Stemmer, W.P.C., "DNA sequence evolution by sexual PCR," 52(abstr.):A25, from 28th Annual Meeting of Swiss Societies for Experimental Biology, Zuerich–Irchel, Switzerland, Mar. 27–29, 1996, abstract S09–04.

Stemmer et al., "Selection of an active single chain FV antibody from a protein linker library prepared by enzymatic inverse PCR," *Biotechniques*, 14(2):256–265 (1993).

Stemmer et al., "Increased antibody expression from *Escherichia–coli* through wobble–base library mutagenesis by enzymatic inverse PCR," *Gene*, 123(1):1–7 (1993).

Stemmer et al., "Enzymatic inverse PCR—a restriction site independent, single–fragment method for high–efficiency, site directed mutagenesis," *Biotechniques*, 13(2):214 (1992).

Stemmer et al., "Expression of antibody FV fragments specific for a heavy metal chelate indium edta in *escherichia–coli*," *J. Cell Biochem.*, suppl 0(15 part G):217, from Meeting on Protein Folding, Structure and Function held at 20th Annual meeting of Keystone Symposia on Molecular and Cellular Biology, Keystone, CO, Apr. 8–14, 1991.

Stemmer, W.P.C., "A 20–minute ethidium bromide high–salt extraction protocol for plasmid DNA," *Biotechniques*, 10(6):726 (1991).

Zhang et al., "Directed evolution of a fucosidase from a galactosidase by DNA shuffling and screening," *PNAS*, 94:4504–4509 (1997).

HPV VECTOR    CONTROL VECTOR

HPV VECTOR    CONTROL VECTOR

HUMAN PAPILLOMA VIRUS VECTORS

CROSS-REFERENCE TO RELATED APPLICATION

The present application is a continuation-in-part of U.S. Ser. No. 08/958,822 filed Oct. 28, 1997, now abandoned, which is incorporated by reference in its entirety for all purposes.

STATEMENT REGARDING FEDERALLY SPONSORED RESEARCH

This invention was made with government support under a Grant No. N65236-98-5401 awarded by the Defense Advanced Research Projects Agency (DARPA). The Government may have certain rights in the invention.

TECHNICAL FIELD

The invention resides in the technical fields of virology and molecular genetics.

BACKGROUND OF THE INVENTION

Papillomaviruses are small, nonenveloped, icosahedral DNA viruses that replicate in the nucleus of squamous epithelial cells. Papillomaviruses consist of a single molecule of double-stranded circular DNA about 8,000 base pairs (bp) in size within a spherical protein coat of 72 capsomeres. Such papillomaviruses are classified by the species they infect (e.g., bovine, human, rabbit) and by type within species. Over 50 distinct human papillomaviruses ("HPV") have been described. See, e.g., Fields Virology (3rd ed., eds. Fields et al., Lippincott-Raven, Philadelphia, 1996).

The DNA of many papillomaviruses, including over 50 human viruses, has been cloned and sequenced. Although there is a high degree of sequence divergence between species, all papillomaviruses share some common features of genome organization. That is, the genome is subdivided into an early region containing proteins E1–E8 (not all are present in all species), a late region, containing genes L1 and L2, and a long control region (LCR) of transcription, including the promoter and enhancer for the viral early genes and the origin of replication. The early region encodes genes required for viral DNA replication, cellular proliferation, and, in some viruses, cellular transformation. The E1 gene and E2 gene encode E1 and E2 polypeptides that bind to the LCR region and induce replication from the origin of replication in the LCR region. The E5, E6 and E7 proteins of the different papillomaviruses have proliferation and sometimes transforming activities. The late region (about 3 kb) codes for the capsid proteins. L1 is the major capsid protein and is relatively well conserved among all the papillomavirus types. The L1 proteins is about 500 amino acids in size. L1 probably induces the major humoral and cell-mediated responses to viral infection. The L2 proteins are about 500 amino acids in size, account for only a small proportion of the virion mass, and their function is not yet clear. The LCR region contains an origin of replication with binding sites for E1 and E2 and other cis acting sequences in the promoter and enhancer region.

Papillomaviruses display a marked degree of cellular tropism for epithelial cells. Specific viral types have a preference for either cutaneous or mucosal epithelial cells. All papillomaviruses have the capacity to induce cellular proliferation. The most common clinical manifestation of proliferation is the production of benign warts. However, many papillomaviruses have capacity to be oncogenic in some individuals and some papillomaviruses are highly oncogenic.

None of the papillomaviruses can be propagated in monolayer cell culture to yield virUs particles, probably because full epithelial differentiation required for production of infectious viral particles is not achieved in conventional cell cultures. However, bovine papillomavirus (BPV) can undergo stable episomal replication in several transformed cells including transformed fibroblasts. Certain anogenital HPVs can grow in organogenic (raft) cultures of epithelial cells (Meyers et al., *Science* 257, 971–973 (1992) and Dollard, et al., *Genes Dev.* 6, 1131–1142 (1992)) but this system requires that one start with cells that harbor already episomal HPV genomes. At present only two such cell lines have been described: the CIN612 line, which harbors highly oncogenic anogenital HPV-31 genomes (Bedell et al, *J. Virol.*, 65, 2254–2260 (1991) and the W12 cell line, which harbors episomal highly oncogenic anogenital HPV-16 genomes (Sterling et al., *J. Virol.* 64, 6305–6307 (1990). Stable replication in cell culture has not been shown so far for any benign cutaneous HPV. Because of the relative difficulties of propagation, most studies of viral lifecycle and protein function have been done in transformed fibroblasts with BPV.

Several authors have discussed papillomaviruses as possible vectors for gene therapy. Ohe et al., *Human Gene Therapy* 6, 325–333 (1995); Woo et al., WO 94/12629 and U.S. Pat. No. 5,674,703 and Xiao & Brandsma, *Nucleic Acids. Res.* 24, 2630–2622 (1996). The attraction of papillomaviruses for this role arises from their persistent but nonfatal state of infection in the human body, their capacity for episomal replication, and their specificity for epithelial cells, which constitute an ideal target for many applications of gene therapy. The challenge in constructing papillomavirus based vectors is to incorporate a coding sequence for a therapeutic product without forfeiting or impairing viral functions that would allow long-term retention and expression of the therapeutic sequence in epithelial cells.

Woo et al., supra, report attempts to construct a bovine papillomavirus (BPV) vector for gene therapy. In a first experiment they reported that a vector containing a marker gene, together with BPV E1 and E2 sequences linked to endogenous BPV promoters, and LCR sequences was unable to replicate in a variety of cell types. However, when the endogenous promoters were replaced with a CMV promoter stable episomal replication was obtained. The authors conclude that the minimal elements for a BPV vector are E1 and E2 coding sequences, a foreign promoter, a BPV origin of replication and a vector maintenance sequence described by Lusky et al., *Cell* 36, 391–401 (1984). The authors speculate that the same approach could be used to produce a human papillomavirus but do not taken into account the different properties and replication capacities of human and bovine viruses. The authors also fail to take into account the lack of sequence similarity between human and bovine papillomaviruses and in particular, the lack of an equivalent to the bovine maintenance sequence of Lusky et al. in human papillomaviruses. Subsequently, it has been reported that the maintenance sequence of Lusky et al. does not appear to contribute to episomal stability even in BPV vectors. Ustav et al., *EMBO* 15, 1–11 (1996).

Ohe et al., *Human Gene Therapy* 6, 325–333 (1995) have reported a bovine papillomavirus vector in which early open reading frames E5, E6 and E7 were deleted. The vector was reported to undergo multicopy episomal replication in a variety of transformed or semitransformed cell types, and to support expression of an exogenous human gene. However, this type of vector is not ideal for gene therapy because it is possible that residual oncogenic activity residues in one of the remaining bovine papillomavirus proteins, and because E1 and E2 proteins are known to be immunogenic (Frattini et al., *EMBO J.* 16, 318–331 (1997)).

Ustav et al., WO 97/24451 also discuss production of a BPV vector for gene therapy. Ustav et al. report that BPV-1 contains 17 E2 binding sites within the LCR region having variable affinity. Ustav et al. propose that a key feature of a BPV vector is a maintenance element including multiple BPV E2 binding sites, of which E2 sites numbered 6, 7 and 8 appear particularly important. However, human papillomaviruses typically have only four E2 binding sites in the LCR element and have no equivalent sequences to BPV E2 binding sites 6, 7 and 8.

The present invention provides vectors derived from a human papillomavirus suitable for expressing a foreign gene in gene therapy.

SUMMARY OF THE INVENTION

The invention provides human papillomavirus vectors useful in gene therapy. Such a vector contains E1 and E2 coding regions from a benign or low risk human papillomavirus operably linked to a promoter and enhancer, and an LCR region from a human papillomavirus comprising an origin of replication including binding sites for the E1 and E2 proteins. The vector also contains a protein coding sequence operably linked to a second promoter and enhancer. In some vectors, the E1 and E2 coding regions are operably linked to their natural promoter and enhancer. In some vectors, the E1 and E2 proteins are from HPV-2, HPV-27 or HPV-57. In some vectors, the E1 and E2 coding regions, the promoter and enhancer, and the LCR region are present in a contiguous segment from HPV-2, -27 or -57 or chimeras thereof. Such cells can be designed to be capable of sustained expression of the protein coding sequence and/or episomal replication in epithelial vectors.

The invention further provides methods for generating and selection of new vector variants with improved properties by DNA shuffling.

The invention further provides methods of gene therapy. The methods entail introducing a vector, as described above, into the skin of a patient. The vector is expressed in cutaneous epidermal cells of the patient to produce the protein. In such methods, the vector is preferably expressed in cutaneous epidermal cells of the patient for at least two weeks. In some methods, the vector is introduced into the patient in naked form or encapsulated in liposomes. The protein to be expressed from such vector may, for example, serve to compensate for a defective human gene, induce a protective immunogenic response. In some methods, the protein to be expressed from the vector is linked to an inducible promoter. In such methods, expression can be controlled by treating a patient with a drug that induces expression. Optionally, the drug can be administered via a patch.

The invention further provides methods of producing an agent for promotion of hair growth or alteration of hair color. Such methods start by shuffling a population of variant forms of a gene encoding a potential agent to produce recombinant forms of the gene. A vector comprising E1 and E2 open reading frames from a cutaneous human papillomavirus (HPV) operably linked to a promoter and enhancer, and an LCR region including an origin of replication, and the recombinant sequences operably linked to a promoter and enhancer is then introduced into human skin present in a human or a nonhuman animal grafted with the human skin. The recombinant sequences are expressed, and expression product(s) thereof with hair-growth promoting activity stimulate growth of hair from the follicles. Vector is recovered from follicles showing hair growth or altered color. The steps are then repeated in an iterative fashion with recombinant sequences from the recovered vector forming the substrates for shuffling until an agent with desired activity of promoting hair growth or altering color has been identified.

BRIEF DESCRIPTION OF THE FIGURES

FIG. 4A: Replication analyses of HPV-57. The HPV-57 plasmid was re-ligated for transfection, after releasing the pUC19 plasmid by EcoRI digest. Lane 1: HPV-57 plasmid isolated from transfected NHEK cells 6 days after transfection, digested with DpnI and linearized with EcoRI. The arrow indicates the undigested and linearized band of HPVs, which have replicated in NHEK cells. Lane 2: untransfected HPV-57 plasmid digested with DpnI and EcoRI. M: 1 kb ladder (Gibco BRL).

A: GFP expression levels one day after transfection. B: GFP expression levels in NHEK cells 7 days after transfection and induced to differentiate 72 hours before plasmid preparation. GFP levels in the control transfected cells declined with time but remained stable in the cells transfected with the HPV vector, and were further upregulated with cellular differentiation.

Figure 7A:
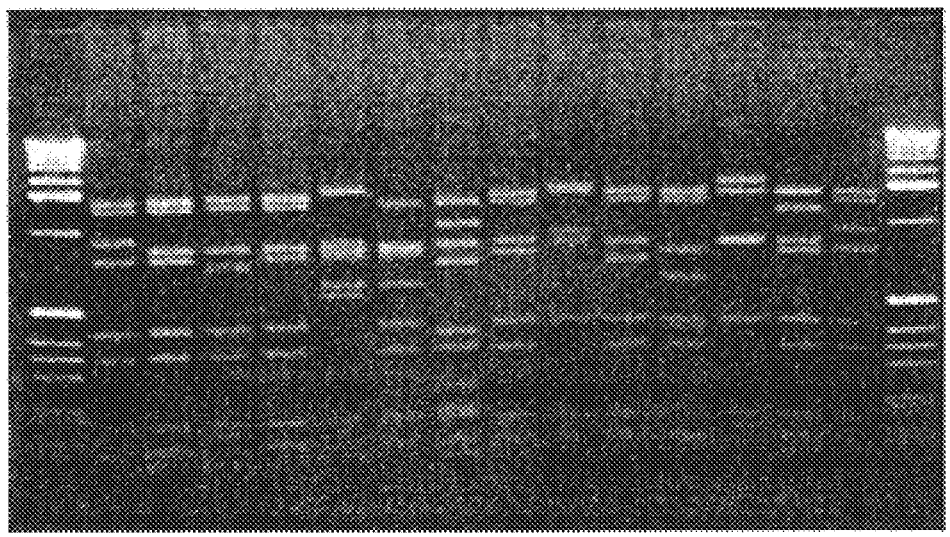
Figure 7B:
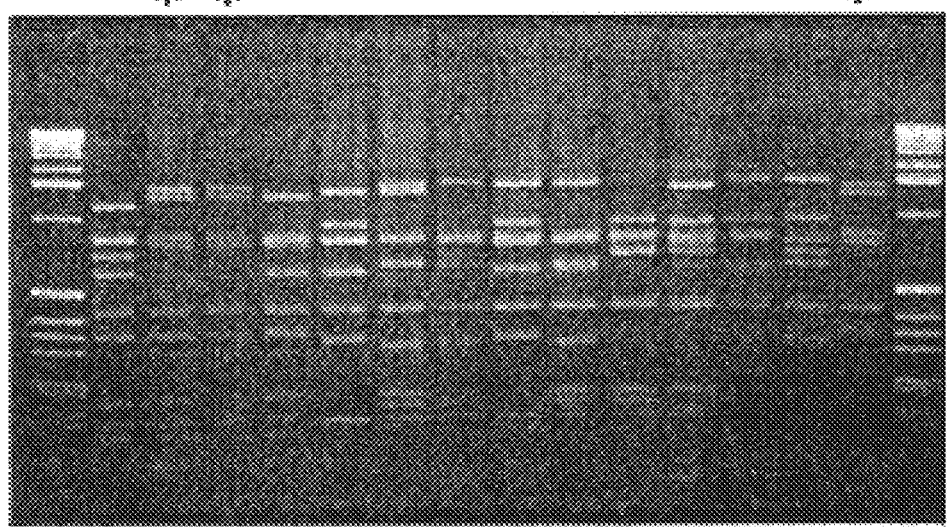

FIG. 7: Restriction analyses of shuffled HPV vector chimeras after replication in NHEK cells. 2 μg of plasmid DNA from shuffled HPV vector libraries was transfected in NHEK cells, rescued after 8 days in culture, digested with DpnI and transformed into *E. coli*. Colony PCR was performed on randomly selected clones with primers spanning the early ORFs and digested with AvaII. The restriction pattern of the HPV-2, 27 and 57 wild type control DNA is shown in the last 3 lanes. Four shuffled HPV vectors were similar to the wildtype HPV-57 pattern (*), 21 clones did not resemble any of the 3 wildtypes.

DEFINITIONS

Screening is, in general, a two-step process in which one first determines which cells do and do not express a screening marker and then physically separates the cells having the desired property. Selection is a form of screening in which identification and physical separation are achieved simultaneously by expression of a selection marker, which, in some genetic circumstances, allows cells expressing the marker to survive while other cells die (or vice versa). Screening markers include luciferase, β-galactosidase, and green fluorescent protein. Selection markers include drug and toxin resistance genes. Although spontaneous selection can and does occur in the course of natural evolution, in the present methods selection is performed by man.

An exogenous DNA segment is one foreign (or heterologous) to the cell or homologous to the cell but in a position within the host cell nucleic acid in which the element is not ordinarily found. Exogenous DNA segments are expressed to yield exogenous polypeptides.

A nucleic acid is operably linked when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. For example, human papillomavirus proteins E1 and E2 are operably linked to an LCR from a human papillomavirus, containing a promoter and enhancer to drive the expression of E1 and E2 and an origin of replication with binding sites for the E1 and E2 proteins.

The term naturally-occurring is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term gene is used broadly to refer to any segment of DNA associated with a biological function. Thus, genes include coding sequences and/or the regulatory sequences required for their expression. Genes also include nonexpressed DNA segments that, for example, form recognition sequences for other proteins.

Figure 1:
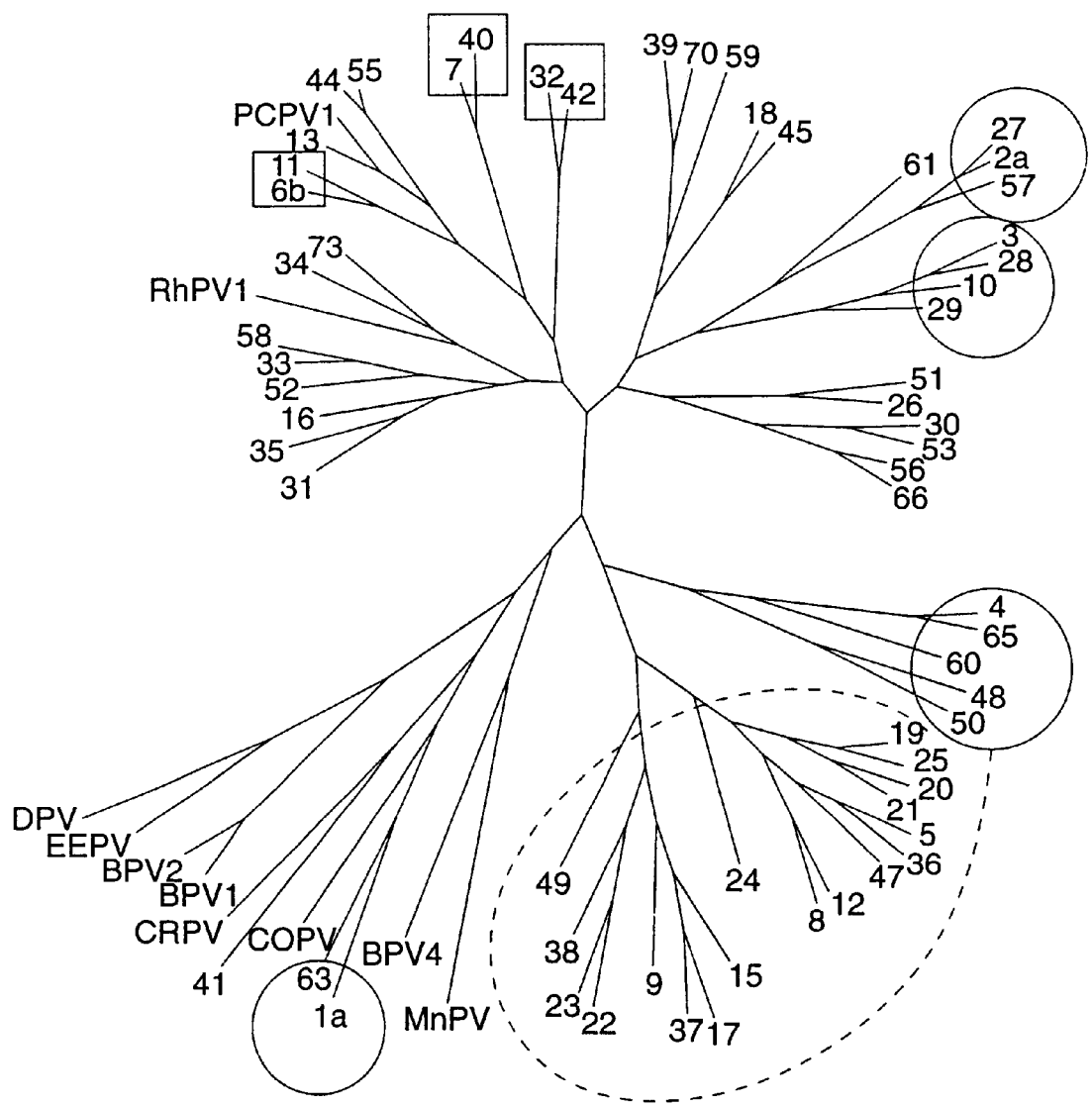
FIG. 1: Phylogenetic tree of papillomaviruses classified by genome sequences. HPVs associated with benign cutaneous or mucosal lesions are circled. Dotted lines show cutaneous HPVs associated with Epidermodysplasia Verruciformis. Low risk orogenital virus are enclosed by square boxes. The other HPV types are of intermediate and high risk with anogenital tropism.

Papillomaviruses are conventionally classified by genome sequence as shown in FIG. 1. The first letter in the designation of papillomavirus (where given) indicates the host. The letter is followed by a number that indicates the type. (Where just a number is given the papillomavirus is an HPV.) Different HPV types in a given branch of the phylogenetic tree are often related with respect to the associated pathogenic lesions. Based on the pathology of the associated lesions, most HPVs can be classified in one of four major groups, benign, low-risk, intermediate-risk and high-risk (*Fields Virology*, (Fields et al., eds., Lippincott-Raven, Philadelphia, 3d ed. 1996); *DNA Tumor Viruses: Papilloma* in (Encyclopedia of Cancer, Academic Press) Vol. 1, p 520–531). For example, viruses HPV-1, HPV-2, HPV-3, HPV-4, and HPV-27 are associated with benign cutaneous lesions. Viruses HPV-6 and HPV-11 are associated with vulval, penile, and laryngeal warts and are considered low-risk viruses as they are rarely associated with invasive carcinomas. Viruses HPV-16, HPV-18, HPV-31, and HPV-45 are considered high risk virus as they are associated with a high frequency with adeno- and squamous carcinoma of the cervix. Viruses HPV-5 and HPV-8 are associated with benign cutaneous lesion in a multifactorial disease Epidermodysplasia Verruciformis (EV). Such lesions, however, can progress into squamous cell carcinomas. These viruses do not fall under one of the four major risk groups. Benign and low risk HPVs are shown enclosed by circles in FIG. 1. Newly discovered HPVs can be classified for risk based on the frequency of cancerous lesions relative to that of HPVs that have already been classified for risk.

DETAILED DISCLOSURE

The invention provides vectors derived from human papillomaviruses. The vectors are particularly suitable for expressing foreign proteins in the skin of human patients.

I. Papillomaviruses

The vectors of the present invention incorporate sequences from human papillomaviruses. Known examples of such viruses include, for example, HPV-1, HPV-2, HPV-3, and HPV-4. The evolutionary relationship of these viruses to each other and to other papillomaviruses is shown in an evolutionary tree in FIG. 1. In general, human papillomavirus with tropism for cutaneous epithelial cells are benign viruses with the exception of EV virus which are also associated with squamous cell carcinomas. HPVs with tropism for cutaneous and mucosal cells are low risk, whereas papillomaviruses with tropism for mucosal cells can be low, medium or high risk. HPV-2 is a preferred source of components because it shows a strong preference for cutaneous tissue and lacks oncogenic potential. HPV-57 is closely related to HPV-2 on the evolutionary tree but infects both cutaneous tissue and mucosal tissue with a preference for the latter. HPV-27 is also closely related to HPV-2 but its tissue preference is unknown. Both HPV-57 and HPV-27 are low risk HPVs. DNA sequences for all of these viruses are described at hppt:\hpv-web.lanl.gov. Variants of a known species exhibiting at least 90% nucleic acid sequence identity in at least three genes (conventionally E6, E7 and L1) are considered to be part of the same species. Variants of known human cutaneous papillomaviruses can be isolated from natural sources or generated by DNA shuffling as described below.

Figure 2:
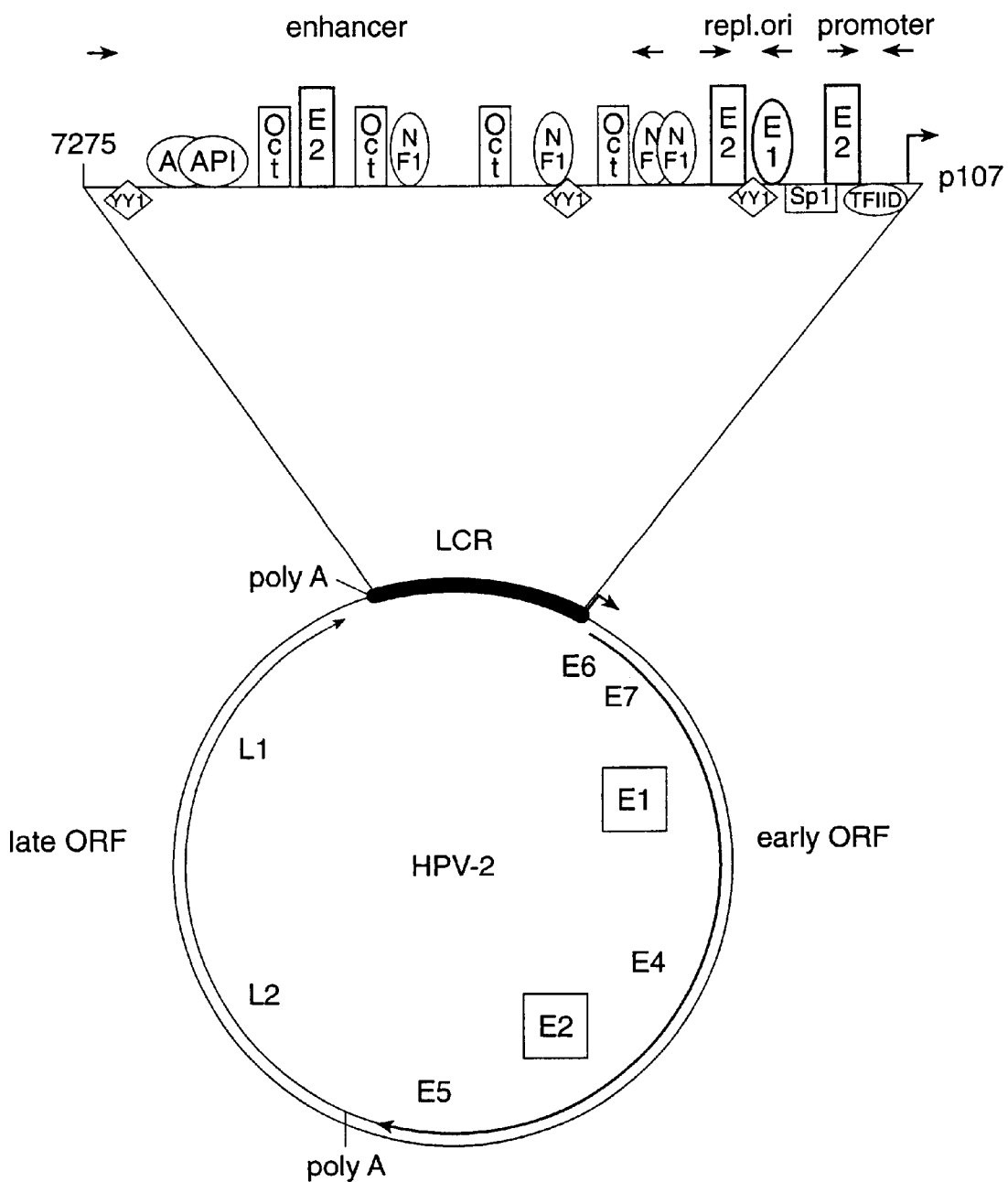
FIG. 2: Map of HPV-2. The HPV 2 early open reading frame includes the genes E1 to E6. The mRNAs are transcribed from the viral long control region (LCR) and are processed by alternative splicing. A blow up of the LCR region shows binding sites for the cellular transcription factors AP1, Oct-1, NFI and YYI in the enhancer region, which regulate cell type specific transcription from the viral promoter, which has binding sites for the cellular transcription factors SP1 and TFIID and two binding sites for the viral E2 protein. Another conserved binding site for E2 is located in the viral enhancer. The origin of replication with binding sites for the viral E1 and E2 proteins is also located within the LCR.

A complete map of the HPV-2 genome is given in FIG. 2. The map shows the viral LCR region, containing the origin of replication, which consists of binding sites for the viral E1 and E2 proteins, three other binding sites for E2, and the viral early promoter/enhancer, driving the expression of the early genes E1, E2, E4, E5, E6, and E7. The messenger RNAs for the viral early proteins are transcribed from the same promoter and processed by alternative RNA splicing. The viral late region codes for the capsid proteins L1 and L2. The positions of open-reading frames and cis-acting sequences were determined by alignment with corresponding sequences from other papillomaviruses using the software DNAstar. The positions of such sequences in other human cutaneous papillomaviruses can be similarly determined.

II. Suitable Cells for In Vitro Experiments

HPV replication is dependent on the expression of the viral early proteins E1 and E2. Transcription of E1 and E2 from the natural promoter/enhancer is epithelial-cell specific. Any epithelial cell line which supports HPV transcription can be potentially used for studies on HPV vectors. Human cervical carcinoma cells like HeLa, Caski, SiHa, C33, or human squamous carcinoma of the tongue like SCC-4, -9, -15, -25, which are available from ATCC, support HPV transcription. It has been shown earlier, that the SCC-cell lines also support transient replication of some anogential HPVs (del Vechio et al., *J. Virol.* 66, 5949–5958 (1992). These cell lines are carcinoma cell lines and can be grown for a unlimited time in tissue culture using standard DMEM medium (BRL) supplemented with 10% FCS. The most suitable cells to study vectors from cutaneous HPVs are, however, primary human keratinocytes (clinical isolates from skin biopsies, or commercially available from Clonetics), the natural hosts and target for gene therapy. Primary keratinocytes can be grown in for a limited number of passages in serum-free media with supplements recommended by the manufacturer (KBM, Clonetics; Keratinocyte SFM, BRL; Medium 154, Cascade Biologiques). When seeded on sub-lethally irradiated or mitomycin-C-treated fibroblast cells, and cultivated in the appropriate medium (Rheinwald & Green, *Cell* 6, 331–344 (1975)) keratinocytes can grow for 50 or more generations in culture and stratify when confluent.

III. Vector Construction

A suitable vector includes E1 and E2 coding sequences from a human papillomavirus operably linked to a promoter and enhancer, an LCR region including at least an origin of replication including binding sites for E1 and E2, and an expression cassette. The E1 and E2 coding sequences are from a benign or low risk human papillomavirus. Examples of such viruses are HPV-1, HPV-2, HPV-3, HPV-4, HPV-6, HPV-7, HPV-10, HPV-11, HPV-27, HPV-28, HPV-29, HPV-48, HPV-50, HPV-57 HPV-60, HPV-63, and HPV-65. The LCR region is from a human papillomavirus but not necessarily a papillomavirus with benign or low risk as the LCR region alone does not confer oncogenic potential. The expression cassette encodes a therapeutic gene and/or marker gene operably linked to a promoter and other regulatory sequences that ensure expression. The E1 and E2 sequences are typically full-length protein coding sequences although sequences encoding fragments can also be used provided the fragments retain similar activity to the full-length sequences. The E1 and E2 vectors are typically linked to the promoter and enhancer with which they are naturally associated. However, other promoters and enhancers can also be used. In this case, the E1 and E2 open-reading frames can be linked to a single promoter/enhancer, as occurs in the HPV-2 genome, or can be separately linked to two promoter/enhancer combinations. To retain the natural tissue tropism of an HPV vector, the promoter/enhancer should be expressed in epithelial cells and preferably exhibit substantial specificity for these cells. Examples of such promoter and/or enhancers besides natural HPV promoter/enhancers include skin-specific promoters such as keratin, E-cadherin, elastin or alpha-1 (I) collagen promoters or ubiquitous promoters such as CMV, RSV, and SV40.

If a vector with altered tissue tropism is required, different promoter/enhancer combinations can be used that preferentially initiate transcription in a tissue of interest. Examples of promoter/enhancers conferring specificity for tissues of possible interest other than epithelial cells include the insulin promoter for pancreatic expression, the creatine kinase promoter for skeletal muscle expression, immunoglobulin heavy chain promoter/enhancer for B-cell expression, albumin enhancer/promoter, tyrosine aminotransferase promoter, transferrin promoter, cytochrome P-450 promoter, apolipoprotein E promoter, apolipoprotein A-1 promoter and β-actin promoter for liver expression, alpha actin, beta myosin heavy chain, myosin light chain, aldolase A for muscle expression; type 4 collagenase, serine dehydratase for lung expression; myelin basic protein, beta amyloid precursor protein, glutamine synthetase, tyrosine hydroxylase for brain expression; globin, immunoglobulin heavy and light chains for blood cell expression; and osteonectin, osteocalcin, osteopontin for bone expression. Alternatively, promoter/enhancers without pronounced tissue specificity can be used, such as an SV40 promoter/enhancer.

The promoter/enhancer in the expression cassette can be from a human papillomavirus or from another source. If from a human papillomavirus, the papillomavirus need not be benign or low risk. The promoter/enhancer should confer expression in the same tissue specificity as the promoter(s)/enhancer(s) from which the E1 and E2 proteins are expressed, and is sometimes but not always specific for that tissue. In some vectors, the expression cassette includes another copy of the same promoter from which E1 and E2 are expressed. In some vectors, the marker or therapeutic gene or both are operably linked to an inducible promoter. Examples of inducible promoter include promoters which can be regulated by steroids, (such as, glucocorticoid or retinoic acid), hormone antagonists (such as RU 486), or are activated by substances not typically present in the human body such as tetracycline or hormones, such as ecdysone. Tetracycline regulates the binding of a mutant tet-repressor (activator) to its binding site in the promoter of the bacterial tet-operon. Gossen et al, *Science* 268, 1766–1769 (1995). Ecdysone regulates the binding of the ecdysone receptor to its binding site in a promoter fragment available from Invitrogen.

The HPV early open reading frames E5, E6, and E7 may or may not be present in the vectors. The early open reading frame E4 overlaps E2 and is therefore at least partially present in the vector of the invention although it is not necessarily expressed in functional form. The open reading frame for L1 and/or L2 are normally entirely or substantially deleted such that functional L1 and L2 proteins are not produced. The L1 and L2 open reading frames are replaced by the expression cassette for expression of the marker gene and/or therapeutic protein. Deletion of L1 and L2 removes the capacity of the vector to reproduce as a virus without impairing capacity for DNA replication. In addition to the E2 binding site present in the origin of replication, one or more of the three other E2 binding sites in HPV can also be present.

The vectors of the invention can also include a procaryotic origin of replication (typically ColE1) or any replication origin which functions in most gram positive and gram negative bacteria) or a yeast origin of replication (for manufacturing in yeast) and a drug selection gene (e.g., ampicillin, kanamycin blasticidin) positioned outside the LCR and early open ring frame components of the vectors. The presence of a procaryotic origin of replication and drug selection gene allows for amplification of large amounts of the DNA in bacterial cells. Kanamycin and blasticidin can be used for drug selection in both *E. coli* and keratinocytes.

Preferred vectors contain a substantially contiguous segment of HPV including the LCR region and the part of the early region including E1 and E2 open reading frames, linked to an expression cassette and a procaryotic origin of replication. The construction of an exemplary vector based on HPV-2 is described in the Examples. The starting material for construction was a cloned form of HPV-2 in which a pBR origin has been inserted into the LCR. The construction of the vector entailed excision of the pBR sequence from the early open reading frame, and excision of late open reading frames L1 and L2. The late open reading frames were then replaced with an expression cassette for expression of an exogenous gene and a pBR origin of replication. The resulting vector thus contains a contiguous segment from HPV including the LCR region and all of the early open reading frames, linked to a pBR origin of replication and an expression cassette comprising a promoter/enhancer (e.g., HPV, CMV, SV40, keratin) and marker gene (e.g., green fluorescent protein, lacZ, luciferase).

Because the vectors of the present invention can typically be administered and propagated/expressed without undergoing packaging into viral form, it is not critical that the overall length of the vector be confined to the natural length of HPV genomes (about 8 kb). Thus, expression cassettes bearing substantial size inserts of 5, 10, 20 or 50 kb can be accommodated.

IV. Characteristics of HPV Expression Vectors

Expression vectors are capable of expressing a therapeutic gene and/or marker gene in their expression cassette in an intended tissue target. Usually, the intended target is skin cells, in which case, the vector is capable of expressing the gene(s) in human skin, in human skin grafted onto a non-human mammal or in a culture of human epithelial cells. Expression occurs for a period of at least 24 hours, a week, a month or six months, or in some vectors, permanently. In some vectors, expression is specific for epithelial cells. That is, such vectors substantially lack capacity for replication and/or expression of genes in other cell types such as fibroblasts. Typically, vectors are capable of episomal replication in a cell without production of viral particles. Vectors lack transforming activity by use of selection of components from a nontransforming HPV, such as HPV-2. Cell proliferation activity may or may not be present depending on whether genes E5–E7 are retained in the vector.

V. Genes for Expression in Gene Therapy

Some methods of gene therapy serve to compensate for a defect in an endogenous gene by integrating a functional copy of the gene into the host chromosome. The inserted gene is expressed at a level to compensate for the defective gene. Diseases amenable to treatment by this approach are often characterized by recessive mutations. That is, both copies of an endogenous gene must be defective for symptoms to appear. The vectors are particularly effective for treating diseases affecting the skin and blood (due to its proximity to the skin), but can also be used for delivering agents to internal organs via diffusion from the skin into the blood, and then to the internal organ. Genetic disease amenable to treatment include cystic fibrosis, sickle cell anemia, $\beta$-thalassemia, phenylketonuria, galactosemia, Wilson's disease, hemochromatosis, severe combined immunodeficiency disease, alpha-1-antitrypsin deficiency, albinism, alkaptonuria, lysosomal storage diseases, Ehlers-Danlos syndrome, hemophilia, glucose-6-phosphate dehydrogenase deficiency, agammaglobulimenia, diabetes insipidus, Lesch-Nyhan syndrome, muscular dystrophy, Wiskott-Aldrich syndrome, Fabry's disease, fragile X-syndrome, and skin diseases such as lamellar ichitiosis, X-linked ichitiosis, junctional epidermolysis and xeroderma pigmentosum.

Other methods of gene therapy serve to express immunogenic epitopes of pathogenic microorganisms, particularly those that infect the skin or can enter the body through the skin. Such microorganisms include clostridia, molluscum contagium, herpes, meningococci, fungi, pseudonomas, staphylococci, and streptococci. For example, the epitopes can be capsid proteins of viruses or outersurface membrane proteins from bacteria. Expression of such proteins induces humoral and/or cellular immune responses that protect against subsequent infection by the microorganism. In some instances, expression of immunogenic epitopes is also useful in a patient already infected with a microorganism in augmenting the host's immunogenic response to the microorganism. Some other applications of HPV vectors for expression of vaccines are as described in copending application U.S. Ser. No. 09/021,769, filed Feb. 11, 1998, and include treatment of autoimmune conditions, inflammation, allergy, asthma, obesity, anorexia, cachexia, and contraception.

Other methods of gene therapy serve to express sequences that encode proteins that are toxic to infecting microorganisms, such as those described above. The effectiveness of antisense molecules in blocking target gene functions or impeding microorganism replication has been demonstrated in a number of different systems (Friedman et al., *Nature* 335, 452–54 (1988); Malim et al., *Cell* 58, 205–14 (1989); Trono at al., *Cell* 59, 113–20 (1989)). Analogous methods are used for suppressing expression of endogenous recipient cell genes encoding adhesion proteins. Suppression of adhesion protein expression in useful in aborting undesirable inflammatory responses, particularly those affecting the skin. Such responses can occur in response to bites by insects, reptiles and other wild or domestic animals. Such responses can also occur in autoimmune diseases affecting the skin, such as lupus erythematosus. Adhesion proteins that can be suppressed by antisense segments present in HPV vectors include integrins, selecting, and immunoglobulin (Ig) superfamily members (see Springer, *Nature* 346, 425–433 (1990). Osborn, *Cell* 62, 3 (1990); Hynes, *Cell* 69, 11 (1992)).

Other applications include the introduction of a functional copy of a tumor suppressor gene into cancerous cell or cells at risk of becoming cancerous, such as described by Lee et al., U.S. Pat. No. 5,532,220. Individuals having defects in one or both copies of an endogenous tumor suppressor gene are particularly at risk of developing cancers. For example, Li-Fraumeni syndrome is a hereditary condition in which individuals receive mutant p53 alleles, resulting in the early onset of various cancers (Harris, *Science* 262, 1980–1981 (1993) Frebourg et al., *PNAS* 89, 6413–6417 (1992); Malkin et al., *Science* 250, 1233 (1990)). Expression of a tumor suppressor gene in a cancerous cell or a cell at risk of becoming cancerous is effective to prevent, arrest and/or reverse cellular proliferation and other manifestations of the cancerous state. Suitable tumor suppressor genes for use in the invention include p53 (Buchman et al., *Gene* 70, 245–252 (1988)), APC, DCC, Rb, WT1, and NF1 (Marx, *Science* 260, 751–752 (1993); Marshall, *Cell* 64, 313–326 (1991)). Vectors bearing a functional copy of a tumor suppressor gene are administered proximal to the intended site of action (e.g., a melanoma or carcinoma).

Other applications include the introduction of a drug-resistance gene to patients undergoing chemotherapy with the drug. The gene is introduced into noncancerous cells to prevent side effects. HPV vectors with tropisms for the skin are particularly suitable for delivery of resistance genes to hair follicles, thereby protecting the hair follicles from the effects of chemotherapy and preventing hair loss in the patient. MDR-1, which encodes a p-glycoprotein that pumps drugs out of the cell (Ching et al., *Adv. Cancer Res.* 60, 157 (1993)) is a preferred drug-resistance gene in such methods.

VI. Routes of Administration

DNA can be administered as a composition in buffered solution or, optionally, as a component of lotions or creams, over extensive areas of skin or to discrete localized areas. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Optionally, chemical modifications of the background of the phosphate backbone can be made to reduce the negative charge allowing free diffusion across the membrane. See Woo et al., WO 94/12629.

In some methods, vectors are administered to desired areas of human skin using a gene gun. See Xiao & Brandsma, supra. The vector bearing a gene of interest is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable.

DNA vectors can also be administered to the skin as components of liposomes. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Liposomes offer several advantages: They are non-toxic and biodegradable in composition; they display long circulation half-lives; and recognition molecules can be readily attached to their surface for targeting to tissues. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The frequency and dose of administration depends on the condition and the patient. For forms of treatment that serve to compensate for genetic deficiencies, lifelong treatment is usually necessary. In other conditions, such as infection by microorganism or inflammation, treatment is usually only necessary until the microorganism has been eliminated or the inflammation has subsided. Expression of the HPV vector can be monitored by inclusion of green fluorescent protein as a marker. Fading of fluorescence of the marker signals the desirability of administering a fresh dose of vector. Effective doses of the compositions of the present invention, for the treatment of the above described conditions vary depending upon many different factors, including means of administration, target site, physiological state of the patient, and other medicants administered. Thus, treatment dosages will need to be titrated to optimize safety and efficacy. Doses ranging from about 10 ng to 1 g, 100 ng to 100 mg, 1 $\mu$g to 10 mg, or 30–300 $\mu$g DNA per patient are typical.

VII. Shuffling of HPV Vectors

HPV vectors of the type described above can be subjected to iterative cycles of recombination and screening (i.e., shuffling) with a view to obtaining vectors with improved properties. Improved properties include increased tissue specificity, altered tissue specificity, increased expression level, prolonged expression, increased episomal copy number, increased or decreased capacity for chromosomal integration, and increased uptake capacity.

The starting materials for shuffling are typically vectors of the kind described above constructed from different strains of human papillomaviruses, or segments or variants of such generated by e.g., error-prone PCR or cassette mutagenesis. The human papillomaviruses, or at least the E1 and E2 coding regions thereof are preferably human cutaneous paillomaviruses. Some formats and examples for DNA shuffling, which can be performed in vitro, in vivo, or both, have been described by the present inventors and co-workers in WO 95/22625; U.S. Pat. Nos. 5,605,793; 5,811,238; WO 96/19256; Stemmer, *Science* 270, 1510 (1995); Stemmer et al., *Gene,* 164, 49–53 (1995); Stemmer, *Bio/Technology,* 13, 549–553 (1995); Stemmer, *Proc. Natl. Acad. Sci. USA* 91, 10747–10751 (1994); Stemmer, *Nature* 370, 389–391 (1994); Crameri et al., *Nature Medicine,* 2(1):1–3, (1996); Crameri et al., *Nature Biotechnology* 14, 315–319 (1996) (each of which is incorporated by reference in its entirety for all purposes). For present purposes, the recombination stage of DNA shuffling is most expeditiously performed using an in vitro format. Two or more starting substrates showing a high degree of sequence identity are converted into overlapping fragments, e.g., from about 5 bp to 1000 bp. The conversion can be effected by a number of different methods, such as DNAseI or RNAse digestion, random shearing or partial restriction enzyme digestion.

Alternatively, the conversion of substrates to fragments can be effected by incomplete PCR amplification of substrates.

The mixed population of nucleic acid fragments are converted to at least partially single-stranded form. Conversion can be effected by heating to about 80° C. to 100° C. to form single-stranded nucleic acid fragments. Single stranded nucleic acid fragments having regions of sequence identity with other single-stranded nucleic acid fragments can then be reannealed by cooling to 20° C. to 75° C. Reannealing generates hybrids of the original substrates having double stranded regions and single stranded overhangs. The single stranded overhangs are then filled in by template-directed extension.

The process of denaturation, renaturation and incubation in the presence of polymerase is repeated typically from about 2 to 100 times. The resulting nucleic acids are a family of double-stranded polynucleotides representing hybrids of the starting substrates. The population of nucleic acids resulting from shuffling is converted to circular form and then used to transform host cells.

After a suitable period for replication and/or expression of transfected vectors, the cells are screened to identify recombinant vectors that confer the property sought to be evolved. The nature of the screen depends on the property. Improved or altered tissue specificity can be screened for by transforming recombinant vectors into a first population of cells for which replication/expression is desired and a second population of cells, for which replication/expression is not desired. For example, the first population might be epithelial cells, and the second cell population fibroblasts. The second cell type is usually present in excess. The two cell types, if they are not readily distinguishable by microscopic examination, can be distinguished by expression of a marker, such as green fluorescent protein or cell surface receptor in one cell type. The cells are then propagated for a period, optionally, under conditions in which vectors can be exchanged between cells. Such conditions can be achieved by application of an electric field. The two cell types are then separated and cells of the desired type retaining and, optionally, expressing a marker gene on the vector are identified. Vectors are recovered from these cells for subsequent rounds of shuffling.

To screen for improved or prolonged expression, recombinant vectors are introduced into cells of a desired tissue type, and after a period, cells with the highest expression level of a marker gene are identified and isolated (e.g., by FACS screening for expression of green fluorescent protein). Vectors are isolated from these cells for the next round of shuffling.

To screen for increased episomal copy number, cells transfected with recombinant vectors are propagated for several generations, and recombinant vectors are recovered from surviving cells. Propagation for several generations automatically enriches for vectors present in the greatest copy number. The recovered vectors are used in the next round of shuffling.

To select for increased capacity for chromosomal integration, cells transfected with recombinant vectors are propagated for several generations. Preferably, the vectors express a selective marker and cells expressing the marker are identified. These cells are then lysed and chromosomal DNA separated from episomal DNA (e.g., by gradient centrifugation). Vectors are then recovered from chromosomal DNA by PCR. The recovered vectors are used in the next round of shuffling.

Vectors with decreased capacity for chromosomal integration can be selected by a similar process. However, in this situation, one recovers episomal DNA after separation from chromosomal DNA, and uses the episomal DNA in the next round of shuffling.

Vectors with improved uptake capacity can be selected by transfecting into cells under transfection conditions similar to those of intended use. For example, if the attended route of therapeutic administration requires liposomes, then liposomes should also be used as vehicles for transfection of cells. Cells expressing a selection marker encoded by the vector are identified. If it is desired to separate effects due to uptake efficiency from other effects that can contribute to expression, such as copy number or regulatory sequences, expression should be detected as soon as possible after transection. Cells expressing the selection marker are isolated and vector recovered from these cells. Recovered vector is used in subsequent rounds of shuffling.

VIII. HPV Vectors for Induction of Hair Growth or Altered Hair Color

HPV vectors such as described above are suitable for screening peptides for efficacy in inducing or stimulating hair growth or in changing hair color. Peptides with activity can then be delivered using an HPV vector. HPV vectors can be initially optimized for delivery of compounds to hair follicles. Hair follicle provide the principal route of entry of DNA molecules, either naked or as components of liposomes, into the skin. See U.S. Pat. No. 5,641,508. Vectors can be evolved to have greater uptake capacity for hair follicles by DNA shuffling. That is, recombinant vectors formed by recombination of related viral vectors as described above are applied, typically in naked form or as liposomes, to an area of human skin. The human skin can be present on a person or can be grafted onto an experimental animal. After a period of time to allow uptake of DNA and replication, DNA is recovered from hair follicles. Optionally, the vectors express a selective marker, and vector DNA is recovered only from hair follicles expressing the selective marker. Vectors recovered from hair follicles are subject to another round of shuffling, and the shuffled vectors are applied to a fresh layer of skin. Performing successive cycles of recombination and selection produces shuffled forms of vectors that have evolved to possess greater capacity to be taken up by hair follicles.

Vectors with evolved uptake capacity are then used to screen polypeptide libraries for efficacy in stimulating hair growth or changing hair color. Particularly preferred are peptides which improve the growth of the hair shaft, agents which stimulate the production of hair coloring pigments in the hair follicle, agents which replace pigment in the follicle cell or hair shaft (i.e., restore hair color), agents which stimulate hair growth, and agents which prevent hair loss. The library of polypeptides can be entirely random or can represent variants of a starting polypeptide suspected to have some activity in promoting hair growth or altering color. For example, polypeptides useful for pigmenting hair color include melanin, which directly colors hair as a pigment, and the protein tyrosinase, which catalyzes the production of melanin pigment precursors, and thereby increases pigment production in hair follicle cells. Starting polypeptides are sometimes obtained by subtractive hybridization of a cDNA library derived from a non-hair-producing tissue from a cDNA library of expressed genes from hair follicle tissue supporting healthy hair, thereby producing a library of cDNA molecules whose expression is specific to hair follicles.

Vectors bearing the library of compounds are applied to human skin grafted onto a mammal or on a human patient. After a suitable time period to allow for gene expression and stimulation of hair growth or alteration of hair color, vectors are recovered from the hair follicles showing the strongest hair growth or closest resemblance to a desired color. The vectors can then be shuffled with each other to generate a library of vectors bearing recombinant forms of a subset of the original library enriched for members having some hair growth stimulating activity. The shuffled library in then applied to fresh skin, and after a suitable time period, vectors are recovered from hair follicles showing the best growth or color as before. After several rounds of recombination and selection, polypeptides with good hair growth stimulating or color-altering properties are identified. HPV vectors expressing one or more such polypeptides are then used as therapeutic agents for restoration or stimulation of hair growth, or alteration of hair color.

IX. Patch Method

Some gene therapy products require transient but repeated administration to a patient. For example, transient expression of an immunogenic epitope may be sufficient to generate a protective response, but this response fades without reinforcement. Further, many inflammatory diseases result in transient flares spread over a long period of time, and expression of therapeutic product may only be necessary during these periods. Similarly, some viruses, such as herpes, which infect the skin do so only transiently, and with prodromal symptoms that provide forewarning of an attack. In such conditions, expression of therapeutic product is necessary only for a short period of time, and prolonged expression may unnecessarily lead to acquisition of resistance.

Controlled transient expression of an HPV vector can be achieved by linking the therapeutic gene to an inducible promoter. The vector is applied to a localized areas of skin by any of the administration routes described previously. The vector is maintained in the skin and may give rise to small warts indicative of HPV infection, but does not express the therapeutic gene without prior administration of an inducer. The inducer is administered by layering a patch impregnated with inducer over the layer of skin in which the HPV vector is replicating. The patches can be of similar composition to those use for transdermal delivery of nicotine (see, e.g., U.S. Pat. No. 5,016,652). The inducer diffuses from the patch to the skin causing expression of the therapeutic gene. Expression of the gene can then be switched off when the supply of inducer provided by the patch is exhausted or when the patch is removed.

EXAMPLES

Example 1

Replication Assay for HPV-2 and HPV-57 Plasmids

The life cycle of human papillomavirus is strongly linked to the differentiation process of the keratinocytes in the skin and replication in cell culture has been demonstrated so far only for BPV and a few orogenital HPVs. The replication competence of benign cutaneous HPV types were tested in primary human keratinocyte tissue grown on fibroblast feeder layer and stimulated to differentiate by elevated calcium and serum levels.

HPV-2 and HPV-57 cloned into pBR vectors were obtained from Dr. E. M. de Villiers, at the Reference Center for Human Papillomavirus, DKFZ, Im Neuenheimer Feld 242, 69120 Heidelberg, Germany. HPV-27 was obtained from Dr. R. Ostrow, Institute of Human Genetics, Box 206 UMHC, Minneapolis, Minn. 55455. Sequences and maps showing the position of genes are given at hppt:\hpv-web.lanl.gov. HPV-2 is cloned into pSP65 using the single EcoRI site at position 1, while HPV-57 is cloned into pUC19 at the single EcoRI site in position 3736, thereby interrupting the long control region (LCR) and the early ORFs. To separate the HPV DNA from bacterial vector sequences, the HPV-2/pSP65 and HPV-57/pUC19 constructs were first digested with EcoRI and the 7.8 kb HPV DNAs were gel purified.

Figure 4A:
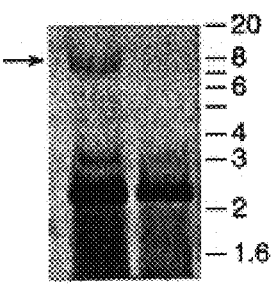
FIGS. 4A, B, C: Replication assay for HPV constructs in normal human epithelial keratinocyte (NHEK) cells. Low molecular weight DNA was extracted from transfected NHEK cells and analyzed by Southern blot, after digestion with DpnI and a single cutting enzyme.
Figure 4B:
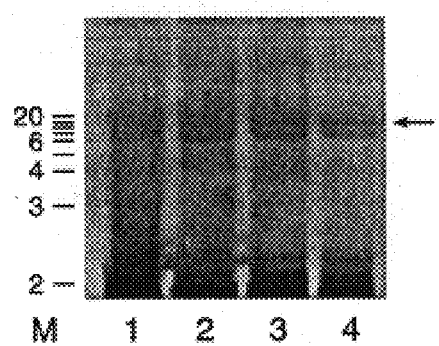
FIG. 4B: Replication analyses of HPV-57 vector constructs. Lanes 1, 2: plasmids isolated from transfected NHEK cells 1 and 3 days after transfection, digested with DpnI and linearized with XbaI. Lanes 3, 4: plasmids isolated from transfected NHEK cells, which were stimulated to differentiate, 3 and 6 days after transfection and digestion with DpnI and XbaI. The arrow indicates an increase of the replicative, linearized form of the vector with time. The undigested band with faster mobility may result from replicative intermediates.
Figure 4C:
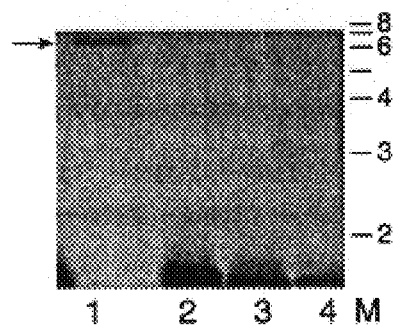
FIG. 4C: The plasmid D/GFP/pUC which contains a dummy sequence instead of the HPV replication unit, was used as control. Lane 1: untransfected plasmid linearized with SacI, lanes 2–4: isolated from transfected NHEK cells 1, 5, and 7 days after transfection, digested with DpnI and SacI.

For transfection, the viral sequences were rejoined in ligation reactions with DNA concentrations of 10 ng/$\mu$l. $2\times10^5$ keratinocytes were tranfected with 2 $\mu$g plasmid DNA using the reagent polybrene (as described below) 18 hr after transfection the keratinocytes were seeded on J2-fibroblast feeder cells (obtained from P. Lambert, University of Wisconsin Medical School, Madison, Wis. 53706) and grown in F-Medium (Flores & Lambert, J. Virol. 71, 7167–7179 (1997) for another 6, 7, or 8 days. 72 hours before harvesting, the cells were stimulated to differentiate by raising the calcium level in the medium to 1.2 mM and the serum level to 10 or 20%. Low molecular weight DNA was prepared (Hirt, J. Mol. Biol. 36, 365–369), digested with the methylation sensitive enzyme DpnI and EcoRI, which linearized HPV-2 and HPV-57 plasmids, and analyzed by Southern blot using standard methods. Analyses for HPV-57 is shown in FIG. 4. DpnI digests only DNA which has been passaged through E. coli thereby acquiring a specific methylation pattern (dam methylation). HPV plasmids that have newly replicated in eucaryotic cells lose their specific methylation pattern and are not digested by DpnI. FIG. 4A, lane 1 shows a band of 7.8 kb that was resistant to DpnI digestion indicative of replication of the HPV-57 plasmid in keratinocytes. Plasmids that have not replicated were digested and gave rise to the restriction pattern of the unreplicated control plasmid (lane 2).

Example 2

Construction and Replication Assay of HPV Vector Backbones

Figure 3A:
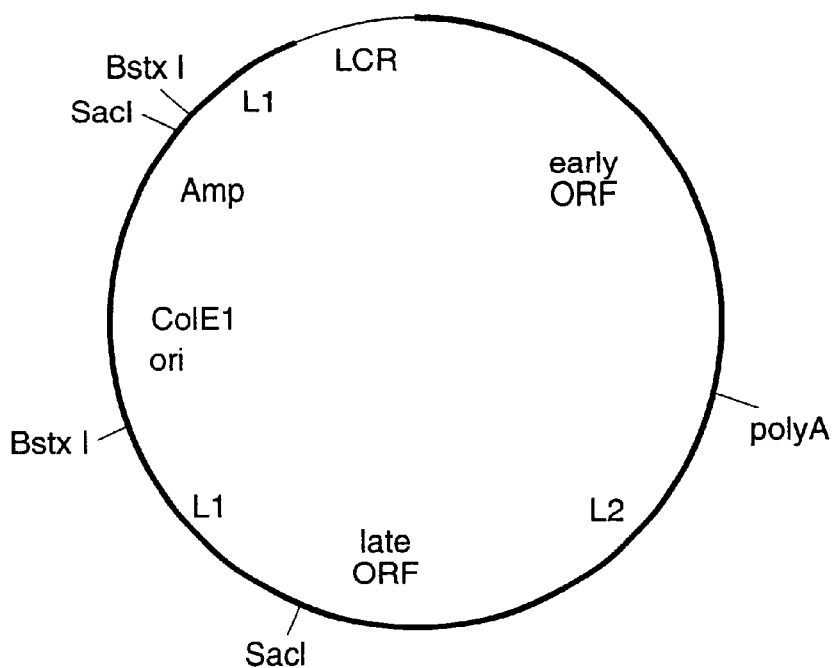
FIG. 3A: An HPV vector construct containing the ColE1 origin of replication and ampicillin resistant gene cloned into the single BstXI site located within the L1 gene of HPV-57. Cloning sites for transgene addition are located in the multiple cloning site of the pUC19 sequence.

A single BstXI site in the L1 gene (HPV-2 position 7145, HPV-57 position 7109) was used to clone the origin of replication and ampicillan resistance gene of pUC19 into the circular HPV genome. The pUC fragment was generated by PCR, BstXI cloning sites were located in the PCR primers (forward primer: 5'-TCTCACTGAACCAATCGATTGGCCGCTTCCTCGC TCACTGACT-3' (SEQ ID NO:1); reverse primer: 5'-AGTCAGTCTCCAATCGATTGGTGCATGCCTCCAG GTCGACTCT-3')(SEQ ID NO:2). The HPV-pUC19 construct of 10.2 kb (FIG. 3A) was transfected into primary human keratinocytes, cultured, rescued and digested with DpnI and XbaI, which linearized the vector construct, as described in example 1. Plasmid DNA was rescued 1, 3, and 6 days after transfection and analyzed by Southern blot. A band of the correct size of about 10 kb appeared at day 3 (FIG. 4, B, lane 2) and increased with calcium stimulation and time (lane 3 and 4).

Figure 3B:
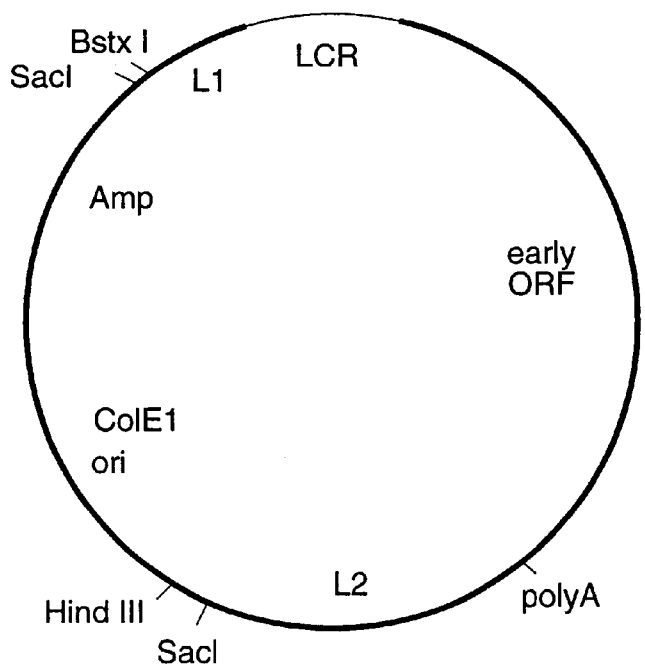
FIG. 3B: An HPV-57 vector construct in which the majority of the L1 ORF is deleted and replaced with the ColE1 origin of replication and ampicillin resistant gene of pUC19. A single BstXI site in the remaining L1 sequences or a single HindIII site included in the pUC sequence 5' of the ColE1 origin can be used for transgene cloning.

The L1 open reading frame, which is dispensable for vector function, was deleted from the vector backbone using SacI restriction sites, located in the polylinker of the pUC19 fragment and at position 5868 in the HPV-57 genome. The pUC fragment was linked back to the truncated HPV-57 plasmid as described above, with SacI cloning sites build in the PCR primers. A HindIII site was designed in the forward primer, which can be used in addition to the single BstXI site, to link transgenes to the vector. The resulting vector construct is 8.8 kb and outlined in FIG. 3B.

Example 3

Construction of an Expression Cassette for Expression in Epidermal Cells and a Control Vector This example describes the construction of an HPV vector for gene therapy starting from a pBR-HPV-2 hybrid in which the pBR moiety occurs within the HPV LCR. The cloning strategy was to isolate the HPV-2 early open reading frame including the viral LCR by PCR and link it to an expression unit containing an epithelial cell-specific enhancer/promoter, driving the expression of a transgene, and optionally, a bacterial origin of replication outside the early region. In the present example, the transgene encodes GFP to allow monitoring, but this can be replaced or supplemented by a gene with therapeutic benefit in actual use.

GFP was used as marker because it can be readily detected by fluorescence microscopy and is also suitable for cell sorting. Gene expression in the skin can be driven by any ubiquitous promoter (CMV, SV40) or, for long term expression, preferentially by an epithelial cell specific promoter. We used a 232 bp fragment of the HPV-16 enhancer linked to an HSV-tk promoter. This construct strongly activates transcription in an epithelial cell specific manner (Chong et al., *J. Virol.* 65, 5933–5943 (1991)). The enhancer-promoter construct was directionally cloned into the HindIII and BamHI sites of pEGFP-1, a promoterless eucaryotic expression vector (Clontec), containing the open reading frame of a GFP with codon usage optimized for human expression and an SV40 poly-A signal.

The newly constructed vector HPV-16e/tkp-pEGFP-1 was tested for GFP expression by transfection into the epithelial cell line SCC-4 (ATCC CRL1624). SCC-4 cells were grown in D-MEM/F12 medium (Gibco BRL), supplemented with 10% FCS and 0.4 $\mu$g/ml hydrocortisone. 24 hr before transfection SCC-4 cells were seeded at a density of 40–60% into 6 well (35 mm) plates. 2 $\mu$g DNA was transfected with Lipofectin reagent (Gibco BRL) in serum-free medium according to the manufacturer's recommendations. After incubation for 7 hr, the medium was changed to serum containing D-MEM/F12 medium, and the cells were incubated for another 12 hr for examination by fluorescence microscopy. At this time period, about 10–20% of the cells gave rise to green fluorescent signals.

For subcloning into the HPV vectors, the GFP expression unit was subsequently isolated from the HPV-16e/tkp-pEGFP-1 construct by PCR. 1 ng of plasmid DNA was used for a 100 $\mu$l PCR reaction containing 2 mM MgCl$_2$, 0.2 mM of each dNTP, 1 unit Taq polymerase (Promega), 0.25 units of Pfu polymerase (Stratagen), and 0.4 $\mu$M of each primer. The PCR primer matching the HPV-16 enhancer on the 5' end contained a Cla I restriction site (5'-TGTGGAAGCTTAAACTTGTACGTTTCCTGCTT-3') (SEQ ID NO:3) and the primer matching the SV40 polyA on the 3' end contained a HindIII restriction site (5'-TCACTATCGATGCCGATTTCGGCCTATTGGTT-3') (SEQ ID NO:4) to allow directional cloning. A PCR program of 25 cycles at 94° C., 30 s, 60° C. 30 s and 72°, 90 s was used. PCR products of 1.47 kb were purified with the QIAquick PCR purification Kit.

Circular HPV-2, 57 and 27 plasmids were used as templates for 100 $\mu$l PCR reaction using the XL PCR amplification Kit (Perkin Elmer) and conditions recommended by the manufacturer. The 5'-HPV PCR primers contained ClaI restriction sites and the 3' PCR primers Hind III restriction sites for ligation to the GFP expression cassette. The forward primers are located at position 7136-7156 (HPV-2), position 7116-7136 (HPV-27), and position 7100-7120 (HPV-57) of the respective HPV genomes. The reverse primers are located at position 4399-4419 (HPV-2), position 4381-4001 (HPV-27), and position 4368-4378 (HPV-57).

Figure 5:
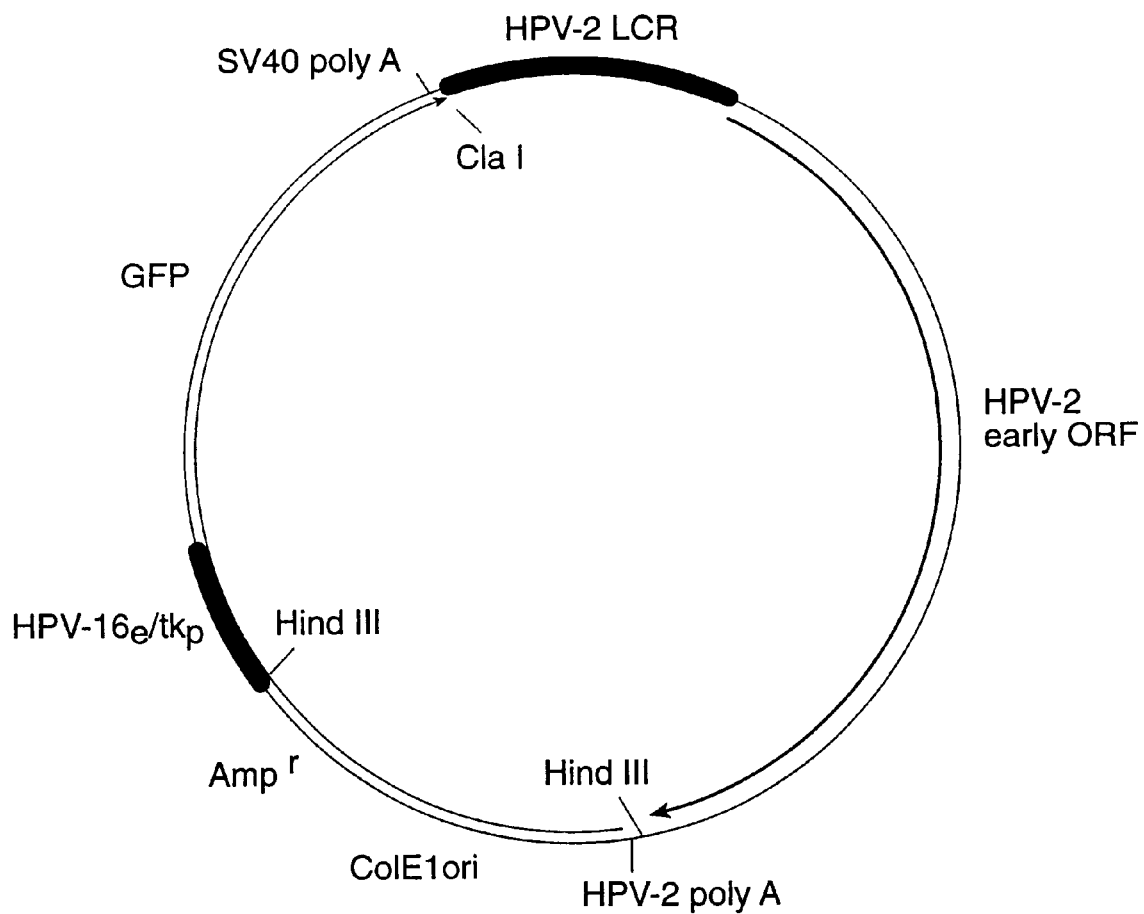
FIG. 5: An HPV derived vector for gene therapy. The vector contains a HPV LCR, early open reading frames and poly A from HPV-2, HPV-27, or HPV-57, a bacterial colE1 origin of replication from pUC19, an ampicillin resistance gene, a second HPV enhancer linked to a minimal thymidine kinase promoter, a green fluorescent protein coding sequence as a marker, and an SV40 poly A sequence.
Figure 6A:
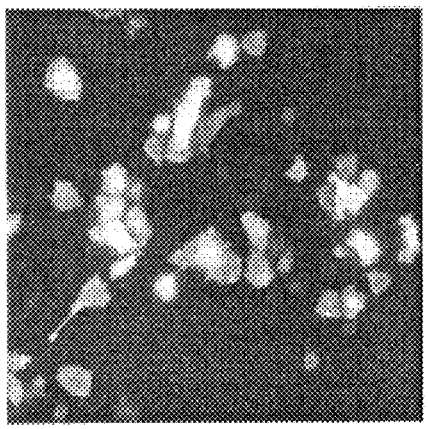
FIGS. 6A, and 6B: HPV vectors confer high GFP expression levels in normal human epithelial keratinocyte (NHFK) cells. NHEK were grown on J2-feeder cells after transfection with an HPV-57 GFP expression vector and a nonreplicating control vector, in which the HPV replication unit was replaced by a dummy sequence.
Figure 6A:
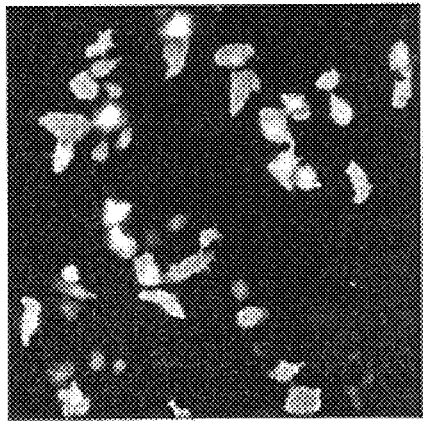
Figure 6B:
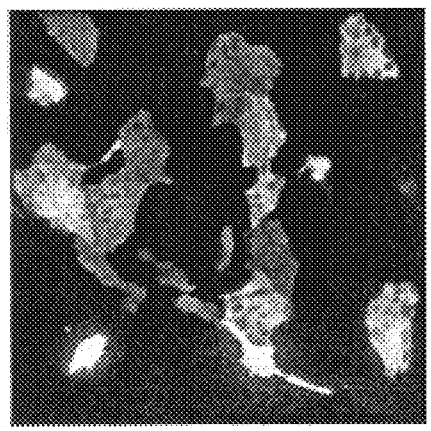
Figure 6B:

The HPV and GFP PCR products were digested for 2 hr with ClaI, QAIquick-column purified, ligated for 2 hrs at RT, digested for 2 hrs with Hind III, and QAIquick column purified. The linear ligated HPV-2/GFP, HPV-27/GFP, and HPV-57/GFP chimeras were then ligated into the HindIII site of pUC19 resulting in a plasmid of 7.8 kb (FIG. 5).

For cell culture transfection, QIAGEN Maxiprep purified total plasmids were used, as well as pUC19-free circular HPV-2 DNA. For these experiments, the HPV-2/GFP DNA was released from the pUC19 sequences by HindIII digestion, gel purified, and religated at a concentration of 10 ng/$\mu$l. This DNA concentration led to monomeric circular ligations. The ligation reactions were QIAquick column purified, ethanol precipitated and dissolved in 10 mM Tris 7.5 for transfection.

Example 4

GFP Expression from HPV Vectors (a) In SCC-4 Cells

Transfections of SCC-4 cells with Lipofectin reagent were performed as described above. As a control for the quantity and duration of GFP expression, the plasmid HPV-16e/tkp-pEGFP-1 was used. This plasmid is based on the vector pEGFP-1 (Clontec) and contains an SV40 origin of replication, which allows episomal replication in cell lines expressing SV40 T-antigen. The plasmid should not replicate in SCC-4 cells, which do not express the SV40-T-antigen, while the newly constructed HPV-vectors are potentially autonomously replicating vectors, containing an origin of replication, which is activated by the viral early proteins E1 and E2, expressed from the same plasmid.

2 $\mu$g each of the control vector HPV-16e/tkp pEGFP-1 and of the HPV-2, -27, -57/GFP constructs were transfected per 35 mm dish. Highest levels of expression for both vectors were detected about 30 hr post transfection. The intensity of the GFP signals, however, varied greatly between the different constructs. While the signal intensity was similar for all three HPV/GFP chimeras, the GFP levels for the non-replicating control vector were about 20–30 fold less. Signal intensity and duration of GFP expression was determined by FACS analysis. GFP signals can be directly measured by using the FL-1 detector. Four days after transfection, the percentage of fluorescent cells in the control population had already markedly dropped, while the HPV/GFP vector transfected cells still expressed the same level of GFP. At day 12 after transfection, the number of fluorescent cells were negligible for the control transfections. The HPV/GFP transfected cells were cultured for another 4 weeks and still showed similar levels of GFP as compared to day 7 post transfection.

b) Primary Human Keratinocytes

SCC-4 cells are transformed tumor cells and the high levels and stability of transgene expression from the HPV vectors may be related to the transformation state of the cells. Therefore, the experiments were repeated in primary human keratinocytes to monitor if a similar advantage of transgene expression and stability could be reached with the HPV vectors in the natural target for gene therapy. Primary human keratinocytes (Clonetics) were transfected with the control vector HPV-16e/tkp pEGFP-1 and the constructs HPV-2, -27, -57/GFP/pUC19 using the reagent Polybrene. 2 ml of serum free keratinocyte medium (Keratinocyte SFM, Gibco BRL) were mixed with 6 $\mu$g DNA and 10 $\mu$l of 1 mg/ml Polybrene-Hexadimethrine bromide (Sigma) in Hanks balanced salt solution. Cells grown in 60 mm dishes at 30% confluency were overlaid with the adsorption cocktail and incubated for 6 hr. The adsorption mix was aspirated and replaced with 4 ml of 28% DMSO in 72% PBS/10% FCS. After 30 seconds, the cells were washed twice with PBS, 10% FCS and further incubated in serum-free keratinocyte medium. Transfection efficiencies of up to 70% could be reached.

The HPV/GFP/pUC constructs gave again rise to 30–50 fold higher GFP levels compared to the non-replicating control vector. At day 7 after transfection, only 20% of the control vector transfectants expressed detectable levels of GFP, while the HPV/GFP/pUC transfected cells remained unchanged. At day 12 after transfection, the percentage of fluorescent cells had also declined for the HPV vectors but showed still a 20-fold improvement of stability compared to the control vectors.

GFP expression from the HPV/GFP/pUC vector and a control vector (D/GFP/pUC) in which the HPV sequences are replaced by a dummy sequence were tested in primary human keratinocytes under growth conditions closely resembling the growth and differentiation conditions in the skin (FIG. 6). Similar transfection efficiencies were achieved for both vectors resulting in similar levels of GFP expression at day 1 (A). GFP levels were, however, significantly higher in the HPV/GFP/pUC vector transfected cells after 6 days in culture on J2-fibroblast feeder cells and calcium stimulation (B).

Example 5

GFP Expression from HPV Vectors in vivo

Human primary keratinocytes were transplanted on severe combined immunodeficiency (SCID) mice and produced histologically and clinically normal multilayer human epidermis (Choate & Khavari, *Human Gene Therapy*, 8, 895–901 (1997). 20 µg of each HPV-2/GFP/pUC and HPV-57/GFP/pUC plasmids were diluted in PBS and directly injected in the human epidermis transplant. PBS was injected as a control. Skin biopsies were taken from regenerated skin xenografts 3 and 7 days after injection. Frozen skin sections were fixed and directly analyzed by fluorescent microscopy. Green fluorescent staining of the epidermis was detected in the injection site for both HPV vectors but not in the control injection sites. GFP levels were similar at day 3 and day 7, which shows that HPV vectors confer stable transgene expression also in vivo.

Example 6

Generation of New Variants of HPV-2, -27 and -57 Early Regions by DNA Shuffling

DNA shuffling is a powerful method to generate new variants in a short time frame. The method involves random fragmentation of the DNA sequences and reassembly by self priming PCR. Crossovers are created in areas of homology, leading to a diversity of chimeric sequences.

The 5 kb early regions of HPV-2, 27, and 57 were amplified from the circular HPV genomes by PCR using PCR primers located 5' of the LCR and 3' of the early ORF poly A sequence. PCR fragments were digested into random fragments of 500–1200 base pairs with DNAseI (Sigma) and electroeluted from a 1.5% agarose gel. The pooled and purified fragments were resuspended at 1 µg/ml in 1×PCR buffer containing 0.2 mM each DNTP, 1.5 mM MgCl2 and 1 U Taq-Polymerase. A PCR program of 15 cycles of 950° C., 60 s; 60° C., 60 s; and 250° C., 120 s was used for the initial assembling reaction. The products of the first assembling reaction were diluted in a PCR buffer containing 0.2 mM each dNTP, 1.5 mM MgOAc, 7% PEG 6000, and 1 U of rTtH polymerase in a buffer system supplied by the manufacturer (XL-Kit, Perkin Elmer). A PCR program of 20 cycles of 94° C., 30 s, 400° C., 30 s, and 72° C., 40 s+2 s/cycle was used for further assembling without primers.

The products of the second PCR reaction were diluted 4× into a new 100 µl PCR mix and the PCR was repeated under the same conditions, to ensure full-length assembled HPV/GFP-pUC products. 1 µl of each of the PCR reactions was then amplified in a 1:100 dilution in a PCR reaction using the XL-kit (Perkin Elmer) according to the of the manufacturer's recommendations. The reaction mix contained 0.2 mM each dNTP, 1.25 mM MgOAc, 2 U of rTtH polymerase and 0.4 M of each primers. The PCR primers were 50 bp in length, located nested to the original primers used for the amplification of the HPV early regions, and contained BstXI cloning sites. Shuffled HPV early regions were ligated back to the unshuffled backbone of the original vector (FIG. 3B) using the BstXI cloning sites. Complex HPV vector libraries with $3\times10^5$–$10^6$ individual clones were generated and screened for improved function.

Example 7

High Efficiency Screening for Episomally Replicating HPV Vectors with Improved Stability and Transgene Expression Primary human keratinocytes plated at 30% confluency in 60 mm dishes were transfected with 8–10 µg of the shuffled HPV-2, -27, and -57 GFP/pUC chimeric constructs. 2–3×10⁵ NHEK cells were transfected with 2–3 µg DNA of the shuffled HPV libraries and grown on fibroblast feeder layer cells (described in example 1) for another 6, 7, 8, or 14 days. Plasmid DNA was harvested, digested with 10 U of DpnI for 16 hr and electroporated into a suitable dam+ *E. coli* strain. Only plasmids which have replicated in transfected NHEK cells are not digested by DpnI and can grow in *E. coli*.

Colonies growing on agar plates after DpnI digest were harvested as pool and plasmid DNA was prepared. The heterogeneity of rescued shuffled HPV vectors after one round of replication in NHEK cells is shown in FIG. 7. The HPV early regions of 25 randomly selected clones were digested with AvaII and compared to the restriction pattern of the HPV wild types (2, 27, 57, last 3 lanes). Only 4 clones resembled the HPV-57 wildtype by AvaII restriction digestion, the other 21 clones analyzed had no similarity with either of the HPV wildtypes. The pool of best sequences from the first round is shuffled again to create a library of recombinants for the next round of selection, from which further improvements can be obtained. Several rounds of selection and passage through primary keratinocytes lead to HPV vectors, which confer the highest transgene expression and stability.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

What is claimed is:

1. A vector comprising:
   a) E1 and E2 coding regions of a benign or low-risk human papilloma virus (HPV) operably linked to a promoter and enhancer; and
   b) a long control region (LCR) of an HPV comprising:
      i) an origin of replication; and
      ii) binding sites for E1 and E2 proteins encoded by said E1 and E2 coding regions;
   wherein the LCR and E1 and E2 coding regions are present in a contiguous segment.

2. The vector of claim 1, wherein the coding regions of E1 and E2 are from a cutaneous HPV.

3. The vector of claim 1, wherein the E1 and E2 coding regions and the LCR are from an HPV selected from the group consisting of HPV-2, HPV-27, and HPV-57.

4. The vector of claim 1, which lacks open reading frame (ORF) L1 and/or L2.

5. A vector comprising:
   a) E1 and E2 coding regions of a benign or low-risk human papilloma virus (HPV) operably linked to a first promoter and enhancer;
   b) a long control region (LCR) of an HPV comprising:
      i) an origin of replication; and
      ii) binding sites for E1 and E2 proteins encoded by said E1 and E2 coding regions;
   wherein the LCR and E1 and E2 coding regions are present in a contiguous segment; and
   c) a nucleic acid sequence encoding an exogenous protein operably linked to a second promoter and enhancer.

6. The vector of claim 5, wherein the coding regions of E1 and E2 are from a cutaneous HPV.

7. The vector of claim 5, wherein the first promoter is the natural promoter of the E1 and E2 coding regions.

8. The vector of claim 5, wherein the E1 and E2 coding regions and the LCR ate from an HPV selected from the group consisting of HPV-2, HPV-27, and HPV-57.

9. The vector of claim 5, which lacks open reading frame (ORF) L1 and/or L2.

10. The vector of claim 5, wherein the second promoter is an inducible promoter.

11. The vector of claim 5, further comprising a second origin of replication which is a bacterial or yeast origin of replication and a nucleic acid sequence encoding a drug selection marker located outside the E1 and E2 coding regions and the LCR.

12. The vector of claim 5 that is greater than 8 kb in length.

13. The vector of claim 5 that replicates episomally in epithelial cells.

14. The vector of claim 5 that is expressed in epthelial cells without being expressed in fibroblasts.

15. The vector of claim 5, wherein the E1 coding region, E2 coding region, and/or the LCR are formed by shuffling of different strains of HPV.

16. The vector of claim 5, wherein the exogenous protein is a therapeutic protein.

17. A vector comprising:
   a) E1 and E2 coding regions of a benign or low-risk human papilloma virus (HPV) operably linked to their natural promoter and enhancer; and
   b) a long control region (LCR) of an HPV comprising:
      i) an origin of replication; and
      ii) binding sites for E1 and E2 proteins encoded by said E1 and E2 coding regions.

18. The vector of claim 17, wherein the E1 and E2 coding regions and the LCR are from an HPV selected from the group consisting of HPV-2, HPV-27, and HPV-57.

19. The vector of claim 17, further comprising a nucleic acid sequence encoding an exogenous protein operably linked to a promoter and enhancer.

20. A vector comprising:
   a) an early open reading frame (ORF) of a benign or low-risk human papilloma virus (HPV) comprising an E1 ORF and E2 ORF each operably linked to a promoter, and
   b) a long control region (LCR) of an HPV comprising:
      i) an origin of replication; and
      ii) binding sites for E1 and E2 proteins encoded by said E1 ORF and E2 ORF,
wherein the LCR and E1 ORF and E2 ORF are present in a contiguous segment.

21. The vector of claim 20, wherein the early ORF further comprises an E4, E5, E6, and/or E7 ORF.

22. A vector comprising:
   a) E1 and E2 coding regions of a benign or low-risk human papilloma virus (HPV) operably linked to a promoter and enhancer;
   b) a long control region (LCR) of an HPV comprising:
      i) an origin of replication; and
      ii) binding sites for E1 and E2 proteins encoded by said E1 and E2 coding regions, wherein the origin of replication and the promoter are present in a contiguous segment.

23. A vector comprising:
   a) E1 and E2 coding regions of a benign or low-risk human papilloma virus (HPV) operably linked to a promoter, and
   b) a long control regions (LCR) of an HPV comprising:
      i) an origin of replication; and
      ii) binding sites for E1 and E2 pins encoded by said E1 and E2 coding regions;
wherein the E1 and E2 coding regions are produced by shuffling an early region of HPV-2, HPV-27, and HPV-57.

24. The vector of claim 23, wherein the early region is about 5 kb in length.

25. A vector comprising:
   a) E1 and E2 coding regions of a benign or low risk human papilloma virus (HPV) operably linked to a first promoter;
   b) a long control region (LCR) of an HPV comprising:
      i) an origin of replication; and
      ii) binding sites for E1 and E2 proteins encoded by said E1 and E2 coding regions;
wherein the E1 and E2 coding regions are produced by shuffling an early region of HPV-2, HPV-27, and HPV-57; and
   c) a nucleic acid sequence encoding an exogenous protein operably linked to a second promoter.

26. A vector comprising:
   a) an E1 coding region of a benign or low-risk human papilloma virus (HPV) operably linked to a first promoter and enhancer;
   b) an E2 coding region of a benign or low-risk human papilloma virus (HPV) operably linked to a second promoter and enhancer; and
   c) a long control region (LCR) of an HPV comprising:
      i) an origin of replication; and
      ii) binding sites for E1 and E2 proteins encoded by said E1 and E2 coding regions;
wherein the LCR and the first or second promoter are present in a contiguous segment.

27. The vector of 26, further comprising a nucleic acid sequence encoding an exogenous protein operably linked to a third promoter and enhancer.

28. A method of expressing an exogenous protein in human skin in vitro comprising:
   introducing a vector into human skin in vitro wherein said vector comprises:
      a) E1 and E2 coding regions of a benign or low-risk human papilloma virus (HPV) operably linked to a first promoter and enhancer;
      b) a long control region (LCR) of an HPV comprising:
         i) an origin or replication; and
         ii) binding sites for the E1 and E2 proteins encoded by said E1 and E2 coding regions; and
      c) a nucleic acid sequence encoding an exogenous protein operably linked to a second promoter and enhancer,
such that the exogenous protein is expressed to a detectable level in at least one cell of said human skin.

29. The method of claim 28, wherein the at least one cell is a cutaneous epidermal cell.

30. The method of claim 28, wherein the exogenous protein is expressed for at least two weeks.

31. The method of claim 28, wherein the vector is in naked form or encapsulated in liposomes.

32. The method of claim 28, wherein the exogenous protein is a human protein.

33. The method of claim 28, wherein the exogenous protein is immunogenic.

34. The method of claim 28, wherein the exogenous protein is toxic.

35. The method of claim 28, wherein the exogenous protein is expressed to a detectable level for at least one month.

36. The method of claim 28, wherein the second promoter is inducible.

37. The method of claim 28, further comprising a second nucleic acid sequence encoding an exogenous protein that is a green fluorescent protein.

38. The method of claim 28, wherein the exogenous protein is a therapeutic protein.

39. The method of claim 28, wherein the at least one cell is an epithelial cell.

40. The method of claim 28, wherein the E1 coding region, E2 coding region, and/or the LCR are formed by shuffling of different strains of HPV.

* * * * *

UNITED STATES PATENT AND TRADEMARK OFFICE
CERTIFICATE OF CORRECTION

PATENT NO. : 6,399,383 B1
DATED : June 4, 2002
INVENTOR(S) : Doris Apt et al.

It is certified that error appears in the above-identified patent and that said Letters Patent is hereby corrected as shown below:

Title page,
Item [56], References Cited, U.S. PATENT DOCUMENTS, add the following U.S. patent reference:

-- 5,674,703    10/1997    Woo et al.    435/69.1 --

FOREIGN PATENT DOCUMENTS, add the following reference:

-- WO    WO 98/07876    2/1998 --

OTHER PUBLICATIONS, add the following reference:

-- Pondel et al., "The LCR-Like α-Globin Positive Regulatory Element Functions As An Enhancer In Transiently Transfected Cells During Erythroid Differentiation", *Nucleic Acids Res.*, 20(2):237-243 (1992). --

Item [75], Inventor, please delete the inventor name "William P. C Stemmer" and insert therefore: -- Willem P.C. Stemmer --

Column 1,
Line 17, please insert the following paragraph:
-- A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. --

Column 22,
Line 66, delete "LCR ate" and insert thereof -- LCR are --.

UNITED STATES PATENT AND TRADEMARK OFFICE
CERTIFICATE OF CORRECTION

PATENT NO. : 6,399,383 B1
DATED : June 4, 2002
INVENTOR(S) : Doris Apt et al.

It is certified that error appears in the above-identified patent and that said Letters Patent is hereby corrected as shown below:

<u>Column 23,</u>
Line 62, delete "regions" and insert therefor -- region --.
Line 64, delete "pins" and insert therefor -- proteins --.

<u>Column 24,</u>
Line 40, delete "origin or" and insert therefor -- origin of --.

Signed and Sealed this

Seventeenth Day of December, 2002

JAMES E. ROGAN
*Director of the United States Patent and Trademark Office*

SEQUENCE LISTING

```
<160> NUMBER OF SEQ ID NOS: 4

<210> SEQ ID NO 1
<211> LENGTH: 43
<212> TYPE: DNA
<213> ORGANISM: Artificial Sequence
<220> FEATURE:
<223> OTHER INFORMATION: Description of Artificial  Sequence:Example 2
      Forward primer

<400> SEQUENCE: 1
tctcactgaa ccaatcgatt ggccgcttcc tcgctcactg act                        43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial  Sequence:Example 2
      Reverse Primer

<400> SEQUENCE: 2
agtcagtctc caatcgattg gtgcatgcct ccaggtcgac tct                        43

<210> SEQ ID NO 3
<211> LENGTH: 32
<212> TYPE: DNA
<213> ORGANISM: Artificial Sequence
<220> FEATURE:
<223> OTHER INFORMATION: Description of Artificial  Sequence:Example 3
      Primer containing Cla 1 restriction  site

<400> SEQUENCE: 3
tgtggaagct taaacttgta cgtttcctgc tt                                    32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial  Sequence: Primer
      containing Hind III restriction sit e

<400> SEQUENCE: 4
tcactatcga tgccgatttc ggcctattgg tt                                    32
```